United States Patent [19]
Spilman

[11] Patent Number: 6,059,803
[45] Date of Patent: May 9, 2000

[54] EAR VACUUM

[76] Inventor: Daniel A. Spilman, 154 Wesley St., Capitola, Calif. 95010

[21] Appl. No.: 09/323,309

[22] Filed: Jun. 1, 1999

[51] Int. Cl.[7] .................................................. A61F 11/00
[52] U.S. Cl. .............................. 606/162; 604/319; 604/35
[58] Field of Search ........................... 606/109, 162; 604/73, 317, 319, 328, 312, 310, 289, 35; 600/200

[56] References Cited

U.S. PATENT DOCUMENTS

| | | | |
|---|---|---|---|
| 4,334,538 | 6/1982 | Juhn | 604/35 |
| 4,684,362 | 8/1987 | Holt | 604/317 |
| 4,712,537 | 12/1987 | Pender | 606/109 |
| 4,915,691 | 4/1990 | Jones et al. | 604/73 |
| 5,062,835 | 11/1991 | Maitz et al. | 604/319 |
| 5,114,415 | 5/1992 | Shedlock | 604/73 |
| 5,665,094 | 9/1997 | Goldenberg | 606/109 |
| 5,843,029 | 12/1998 | Bachman et al. | 604/73 |

*Primary Examiner*—Gene Mancene
*Assistant Examiner*—Eduardo C. Robert
*Attorney, Agent, or Firm*—Jeffrey A. Hall

[57] ABSTRACT

A portable hand held ear vacuum device, for removing fluid and debris from an ear canal, comprising a handle element with a motor linked to a fan and a control switch. A collection chamber for collecting fluid and other debris from an ear canal is secured to the handle element. The collection chamber has a reservoir therein for collecting and storing accumulated fluid and debris from the ear canal. An ear insertion element is secured to the collection chamber. The ear insertion element has an aperture therein, the aperture being continuous with the reservoir in the collection chamber. The motor in the handle creates a vacuum within the collection chamber, enabling fluids and debris to be drawn from the ear canal into the reservoir by suction.

12 Claims, 1 Drawing Sheet

EAR VACUUM

BACKGROUND OF THE INVENTION

1. Field of Invention

This invention relates to devices for removing fluid and debris from the ear canal by use of a hand held vacuum device.

2. Description of the Related Art

Heretofore, numerous devices have been proposed and implemented for extracting fluids, particulates, and other matter from different orifices and tissues of human and animal bodies. Although useful for some applications, such devices are severely limited when applied to the task of removing fluid, particulates or other debris from the human ear.

The ear canal is prone to collection of water after swimming, diving, surfing, and the like, and accumulation of wax, and development of infections resulting in discharge are common. Non-mechanical hand held curettes have been the traditional method of wax removal by physicians. Fluid removal is typically performed in a physician's office by using large electrical powered vacuum pumps connected to tubing to narrow gauge tips under direct visualization to evacuate fluid and debris. Cotton tipped swabs are often used inappropriately in the ear canal to remove wax and fluid, however, such use can cause trauma to the tissues of the ear as well as worsen the impaction of fluid and debris.

Accordingly, the present invention provides a novel device which enables a person without specific medical training to safely remove fluid and debris from the ear canal without causing trauma to the eardrum or skin of the ear canal. The device of the present invention is portable, lightweight, inexpensive to manufacture, and highly efficient at removing fluid, wax, and other debris from the ear canal.

Additional objects and advantages of the invention will be set forth in the description which follows, and in part will be obvious from the description, or may be learned by practice of the invention. The objects and advantages of the invention may be realized and obtained by means of the instrumentality's and combinations particularly pointed out in the appended claims.

BRIEF SUMMARY OF THE INVENTION

The present invention is a safe and reliable device for removing fluid and debris from the ear canal without causing injury to the ear canal or related tissues, and that is easily used by individuals without specific medical training.

Accordingly a portable hand held ear vacuum device is provided, for removing fluid and debris from an ear canal, comprising a handle element with a motor linked to a fan and a control switch. A collection chamber for collecting fluid and other debris from the ear canal is secured to the handle element. The collection chamber has a reservoir therein for collecting and storing accumulated fluid and debris from the ear canal. An ear insertion element is secured to the connecting neck and to the collection chamber. The ear insertion element has an aperture therein, the aperture being continuous with the reservoir in the collection chamber. The motor in the handle creates a vacuum within the collection chamber, enabling fluids and debris to be drawn from the ear canal into the reservoir by suction.

The device is placed into the ear canal and the power switch is activated. A vacuum is generated which draws fluid and particles into the barrel of the device and deposits them in the collecting chamber. A ball valve or water impermeable membrane in the collecting chamber prevents fluid from entering the vacuum motor and damaging it. The ear insertion element, connecting neck, and collection chamber are removable, thereby enabling easy cleaning and exchange of parts for different sized ears.

BRIEF DESCRIPTION OF THE DRAWINGS

The accompanying drawings, which are incorporated in and constitute a part of the specification, illustrate a preferred embodiment of the invention and, together with a general description given above and the detailed description of the preferred embodiment given below, serve to explain the principles of the invention.

DETAILED DESCRIPTION OF THE INVENTION

Reference will now be made in detail to the present preferred embodiments of the invention as illustrated in the accompanying drawings.

In accordance with the present invention, there is provided a portable hand held ear vacuum device, for removing fluid and debris from an ear canal, comprising a handle element with a motor linked to a fan and a control switch. A collection chamber for collecting fluid and other debris from an ear canal is secured to the handle element. The collection chamber has a reservoir therein for collecting and storing accumulated fluid and debris from the ear canal. An ear insertion element is secured to the collection chamber. The ear insertion element has an aperture therein, the aperture being continuous with the reservoir in the collection chamber. The motor in the handle creates a vacuum within the collection chamber, enabling fluids and debris to be drawn from the ear canal into the reservoir by suction.

Figure 1:
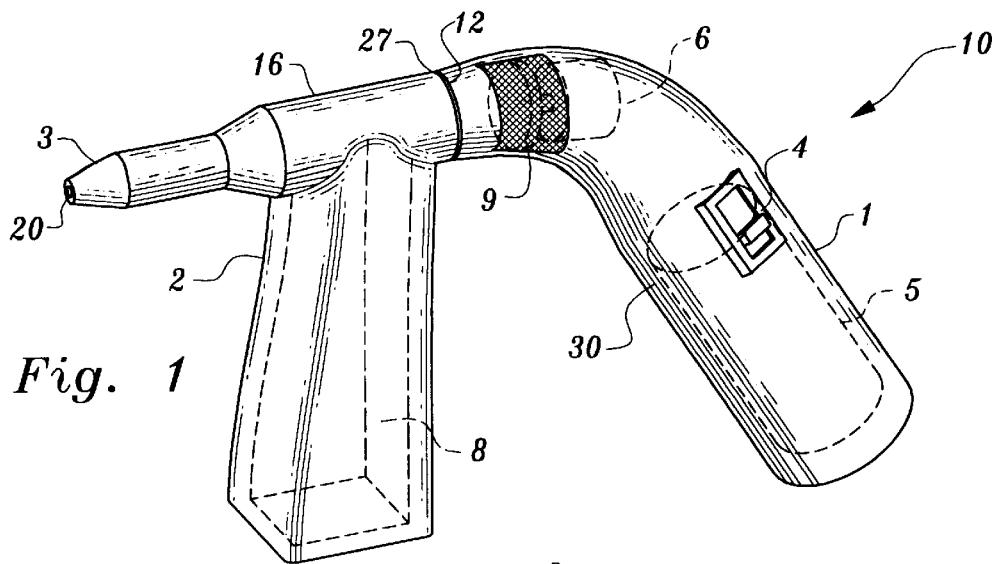
FIG. 1 is a perspective view of the ear vacuum device, according to the invention.

In FIG. 1, an ear vacuum device 10, for removing fluid, wax and other debris from the ear canal, is shown according to a preferred embodiment of the invention. Device 10 is preferably includes a handle 1, which contains the power supply, preferably a battery 5, control switch 4, and motor 6. Control switch 4 is operably linked to motor 6 and battery 5 by wire 25. A collection chamber 2, for collecting fluids, wax, and other debris from the ear canal is detachably secured to handle 1 by a locking thread 27, however, other means of attachment are also possible, such as mechanical fastening means, welds, or alternatively, providing collection chamber 2 and handle 1 as a single non-separable unit.

Figure 3:
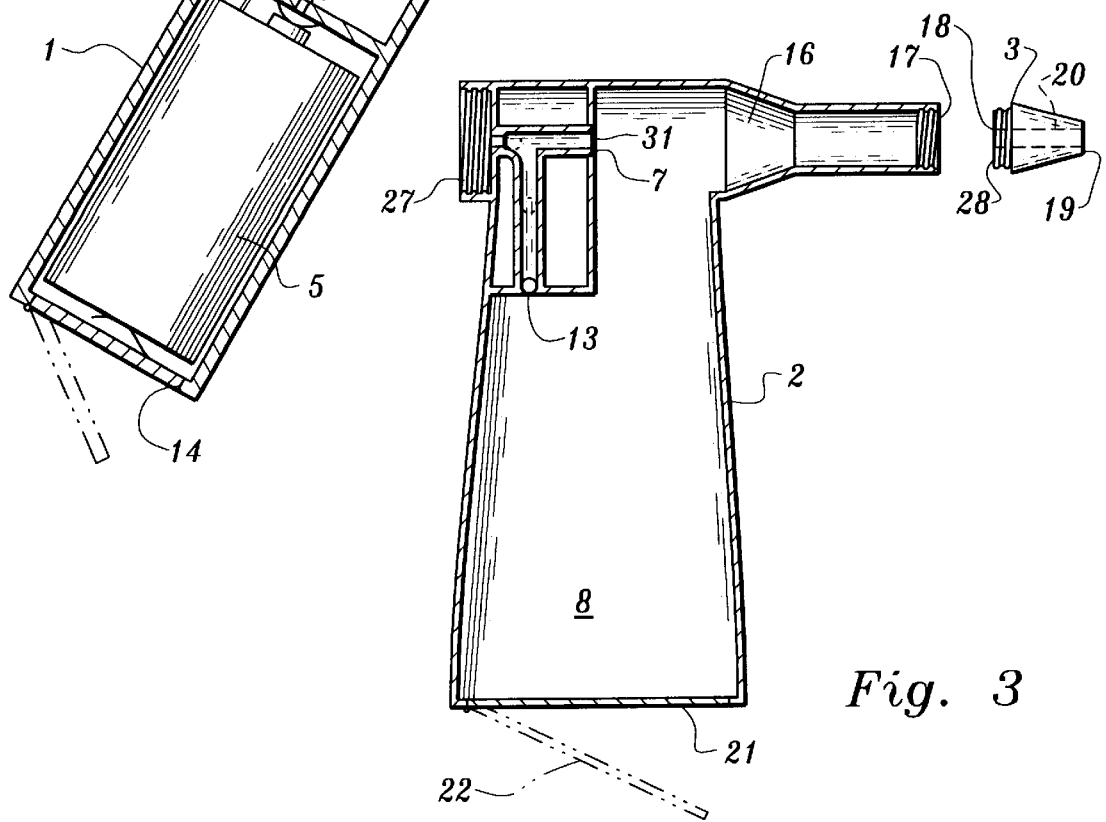
FIG. 3 shows a cut-away view of the collection chamber of such device, according to the invention.

Collection chamber 2 preferably contains a reservoir 8, and a ball valve 13, best seen in FIG. 3, or water impermeable membrane 31. Or it is possible, but not necessary, to include both a ball valve 13, and water impermeable membrane 31 together. An ear insertion element 3 is detachably secured to collection chamber 2, preferably by a locking thread 28. Ventilation panels 9 are preferably positioned on both sides of handle 1 as seen in FIG. 1.

Figure 2:
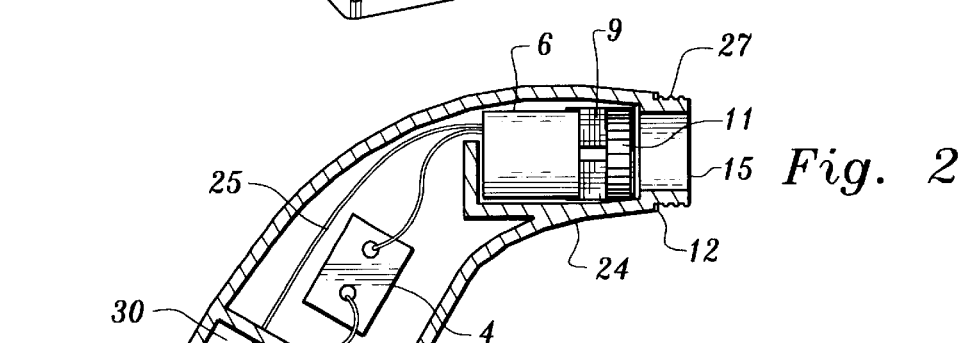
FIG. 2 is a cut-away view of the handle of such device, according to the invention.

With reference now to FIG. 2, details of handle 1 are illustrated. Handle 1, preferably contains a compartment 30, for batteries 5, or other power supply means. Preferably, batteries 5 insert through aperture 14, and are connected to wire 25 and to control switch 4 and motor 6. Motor housing 24, houses motor 6 which is operably connected to intake fan 11 which draws a negative pressure through connecting neck 15 of motor housing 24. A gasket 12 enables collection chamber 2 to be sealed when connected to handle 1. Intake fan 11 rotates when activated by motor 6 thereby drawing in a negative pressure via connecting neck 15, which is operably connected to a tube 7, in collection chamber 2.

In FIG. 3, collection chamber 2, is shown with one way ball valve 13. Alternatively, a water impermeable membrane 31 may be used, or both. Either the one way ball valve 13 or the water impermeable membrane 31 is continuous with connecting neck 15. Water impermeable membrane 31 is communicativley linked with connecting element 16. Locking threads 17 connect to threads 28 of ear insertion element 3. A door 22, is preferably provided which enables collection chamber 2 to be emptied and cleaned via aperture 21. Ear insertion element 3, is preferably a conical hollow piece which connects via threads 28, on side 18 to collection chamber 2. Ear insertion element 3, may be provided in various sizes, and is preferably inserted into the ear from end 19 with aperture 20.

In operation and use, ear vacuum device 10, is simply held in the users hand and then ear insertion element 3 inserted into an ear canal. Control switch 4 is engaged which activates motor 6 and intake fan 11. This creates a vacuum within ear collection chamber 2 and ear insertion element 3, thereby withdrawing fluid, wax, and other debris from the ear canal.

As is evident from the above description, a wide variety of ear vacuum devices may been envisioned from the device described herein and additional advantages and modifications will readily occur to those skilled in the art. The invention in its broader aspects is, therefore, not limited to the specific details, representative apparatus and illustrative examples shown and described. Accordingly, departures from such details may be made without departing from the spirit or scope of the applicant's general inventive concept.

What is claimed is:

1. An ear vacuum device, for removing fluid and debris from an ear canal, comprising:

a handle element;

a collection chamber for collecting fluid and other debris from an ear canal; said collection chamber being operably secured to said handle element; the collection chamber having a reservoir therein for collecting and storing accumulated fluid and debris from the ear canal and a water impermeable membrane operably positioned therein;

an ear insertion element, said ear insertion element being secured to said collection chamber; the ear insertion element having an aperture therein, said aperture being continuous with said reservoir in the collection chamber; and a motor secured within said handle operably and linked to a power supply, said motor creates a vacuum within the collection chamber when activated, enabling fluids and debris to be drawn from the ear canal into said reservoir by suction.

2. The ear vacuum device of claim 1, wherein said motor is operably linked to a control switch positioned on said handle.

3. The ear vacuum device of claim 2, wherein said motor is operably linked to an intake fan.

4. The ear vacuum device of claim 1, wherein said power supply is a battery.

5. The ear vacuum device of claim 1, wherein said water impermeable membrane is operably linked to a connecting element and positioned within said collection chamber.

6. The ear vacuum device of claim 1, wherein said collection chamber includes a ball valve positioned within a connecting neck element within said collection chamber.

7. The ear vacuum device of claim 1, wherein said collection chamber further includes a door element covering an aperture, allowing said collection chamber to be cleaned.

8. A portable hand held ear vacuum device, for removing fluid and debris from an ear canal, comprising:

a handle element;

a collection chamber for collecting fluid and other debris from an ear canal; said collection chamber being operably secured to said handle element; the collection chamber having a reservoir therein for collecting and storing accumulated fluid and debris from the ear canal, the collection chamber includes a water impermeable membrane positioned within said collection chamber;

an ear insertion element, said ear insertion element being secured to said collection chamber; the ear insertion element having an aperture therein, said aperture being continuous with said reservoir in the collection chamber; and a motor for creating a vacuum within the collection chamber, enabling fluids and debris to be drawn from the ear canal into said reservoir by suction.

9. The ear vacuum device of claim 3, wherein said motor for creating a vacuum within the collection chamber comprises a battery powered motor secured within said handle operably and linked to a power supply.

10. The ear vacuum device of claim 3, wherein said motor is operably linked to a control switch positioned on said handle.

11. The ear vacuum device of claim 3, wherein said collection chamber includes a ball valve positioned within a connecting neck element within said collection chamber.

12. The ear vacuum device of claim 3, wherein said collection chamber further includes a door element covering an aperture, allowing said collection chamber to be cleaned.

\* \* \* \* \*